US00PP29311P2

(12) United States Plant Patent
Danziger

(10) Patent No.: US PP29,311 P2
(45) Date of Patent: May 22, 2018

(54) ***PETUNIA* PLANT NAMED 'DPECLABRAY'**

(50) Latin Name: *Petunia hybrida*
Varietal Denomination: DPECLABRAY

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days. days.

(21) Appl. No.: 15/731,167

(22) Filed: Apr. 26, 2017

(51) Int. Cl.
*A01H 5/02* (2018.01)

(52) U.S. Cl.
USPC ..... Plt./356.16
CPC ..... *A01H 5/02* (2013.01)

(58) Field of Classification Search
USPC ..... Plt./356.16
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Petunia* cultivar named 'DPECLABRAY' is disclosed, characterized by a mounded growth habit. The plants are very well branched with medium vigor. The flower color is light blue. The flowers are large and plants flower abundantly. The new variety is a *Petunia*, normally produced as an outdoor garden or container plant.

2 Drawing Sheets

Figure 1:
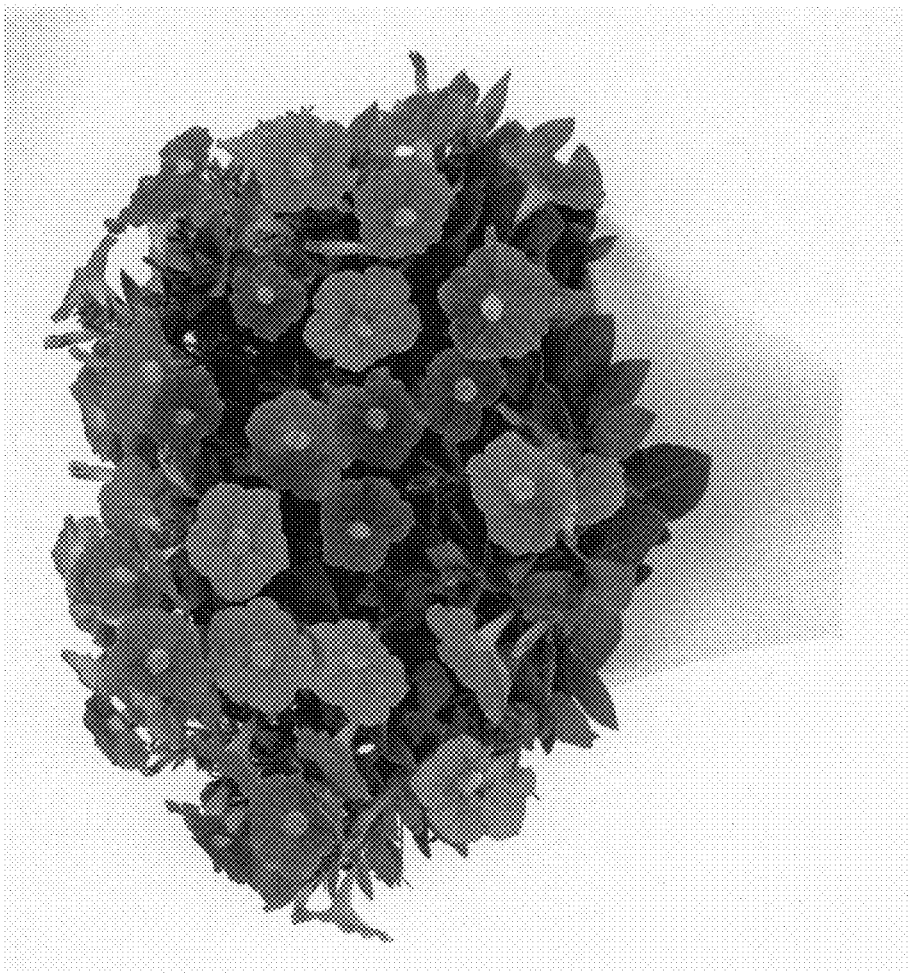

Latin name of the genus and species: *Petunia hybrida.*
Variety denomination: 'DPECLABRAY'.

BACKGROUND OF THE INVENTION

The new *Petunia hybrida* cultivar is a product of a planned breeding program conducted by the inventor, Gavriel Danziger in Moshav Mishmar Hashiva, Israel. The objective of the breeding program was to produce new *Petunia* varieties for ornamental purposes. The cross resulting in this new variety was made during October of 2013.

The seed parent is the unpatented, propriety variety referred to as *Petunia* 'cv. 13-7456'. The pollen parent is the unpatented, propriety variety referred to as *Petunia* 'cv. 13-7686'. The new variety was discovered in July of 2014 by the inventor in a group of seedlings resulting from the 2013 crossing, in a greenhouse in Moshav Mishmar Hashiva, Israel.

Asexual reproduction of the new cultivar 'DPECLABRAY' was first performed by terminal vegetative cuttings during July of 2014, at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DPECLABRAY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPECLABRAY' These characteristics in combination distinguish 'DPECLABRAY' as a new and distinct *Petunia* cultivar:

1. Mounded growth habit.
2. Very well branched plants with medium vigor.

3. Flower color is light blue.
4. Flower size is large.
5. Abundant flowering.

PARENT COMPARISON

Plants of the new cultivar 'DPECLABRAY' are similar to plants of the seed parent, *Petunia* 'cv. 13-7456' most horticultural characteristics, however, plants of the new cultivar 'DPECLABRAY' differ in the following;

1. The new variety is mounded in plant habit, the seed parent is an pright plant.
2. The new variety is less vigorous in growth, but, with more branches
3. Flower color of the new variety is blue, the seed parent is blue with black veins.
4. Flower size of the seed parent is medium, flower size of the new variety is large.
5. The new variety flowers more abundantly.

Plants of the new cultivar 'DPECLABRAY' are similar to plants of the pollen parent, *Petunia* 'cv. 13-7686' most horticultural characteristics however, plants of the new cultivar 'DPECLABRAY' differ in the following;

1. The pollen parent has a semi-trailing plant, the new variety is mounded.
2. The new variety is more vigorous and produces more branches per plant.
3. Flower color of the new variety is darker blue, the pollen parent is very light blue.
4. Flower size of the pollen parent is extra-large, the new variety has a large flower.
5. The new variety flowers more abundantly.

COMMERCIAL COMPARISON

Plants of the new cultivar 'DPECLABRAY' can be compared to the unpatented commercial variety *Petunia* 'Purple Vein Ray'. These varieties are similar in most horticultural characteristics; however, 'DPECLABRAY' differs in the following:

1. Flower size of the comparator is larger than the flower of the new variety
2. Flower color of the comparator is violet with purple veins, while the new variety has light blue flowers.
3. Leaves of this comparator are smaller than the leaves of the new variety.
4. Flower throat color of this comparator is dark purple, while the new variety's flower has a white throat.

Plants of the new cultivar 'DPECLABRAY' can also be compared to the unpatented commercial variety 'Purple Ray'. These varieties are similar in most horticultural characteristics; however, 'DPECLABRAY' differs in the following:

1. Flower size of this comparator is larger than the flower of the new variety.
2. Flower color of this comparator is purple, while the new variety has light blue flowers.
3. Plant vigor of this comparator is stronger than the vigor of the new variety.
4. Flower throat color of this comparator is blue with dark veins, while the new variety's flower has a white throat.

BRIEF DESCRIPTION OF THE PHOTOGRAPHS

The accompanying photograph in FIG. 1 illustrates in full color a typical plant of 'DPECLABRAY' grown in a greenhouse, in Moshav Mishmar Hashiva, Israel.

Figure 2:
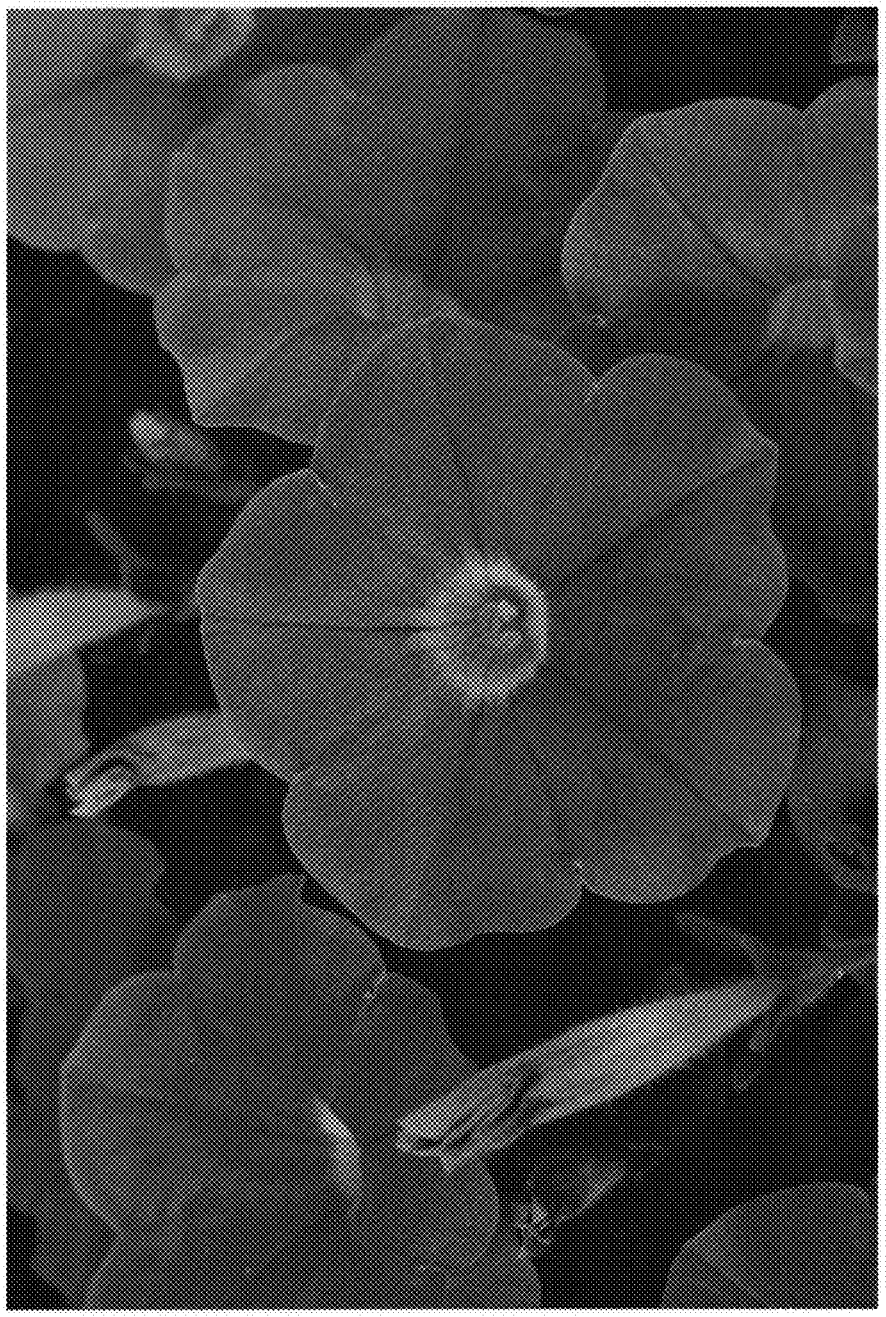

FIG. 2 illustrates in full color typical mature flowers of 'DPECLABRAY' during Spring. Age of the plant photographed is approximately 90 days from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPECLABRAY' plants grown in greenhouse in Moshav Mishmar Hashiva, Israel, under natural lighting. Measurements were taken during April of 2015. The plants were approximately 90 days from a rooted cutting in a 13 cm pot. The growing temperature ranged from 20° C. to 35° C. during the days, 17° C. to 23° C. during the nights. Measurements and numerical values represent averages of typical plant types.

Botanical classification: *Petunia hybrida* 'DPECLABRAY'.

PROPAGATION

Time to Initiate Roots: 10-14 days at approximately 20° C.

Root description: Fibrous. Colored tan and white, not accurately measured with R.H.S. chart.

PLANT

Growth habit: Mounded.

Pot size of plant described: 13 cm.

Height: To top of flowers: about 22 cm.

Plant spread: About 50 cm.

Growth rate: Medium.

Branching characteristics: Very branched.

Length of primary lateral branches: About 25 cm.

Diameter of lateral branches: About 0.4 cm.

Quantity of primary lateral branches: 8.

Characteristics of primary lateral branches:

*Form*.—Cylindrical.
*Diameter*.—About 0.4 cm.
*Color*.—RHS Yellow-Green 145 B.
*Texture*.—Pubescent.
*Strength*.—Good.

Internode length: About 1.5 cm.

FOLIAGE

Leaf:

*Arrangement*.—Opposite.
*Quantity*.—Approximately 20 per branch.
*Average length*.—6.0 cm.
*Average width*.—4.0 cm.
*Shape of blade*.—Elliptic.
*Apex*.—Acute.
*Base*.—Broadly tapered.
*Margin*.—Entire.
*Texture of top surface*.—Velvety.
*Texture of bottom surface*.—Velvety.
*Color*.—Young foliage upper side: RHS Green 137 A. Young foliage under side: RHS Green 136 A. Mature foliage upper side: RHS Green 137 B. Mature foliage under side: RHS Yellow-Green 146 B.
*Venation*.—Type: Pinnate. Venation color upper side: RHS Yellow-Green 146 B. Venation color under side: RHS Yellow-Green 146 C.
*Petiole*.—Length: About 0.8 cm. Diameter: About 0.6 cm. Color: RHS Yellow-Green 146 B. Texture: Velvety.

FLOWER

Natural flowering season: Spring, Summer and Autumn.

Days to flowering from rooted cutting: About 30 days.

Inflorescence and flower type and habit: Axillary, single flower, salverform shape, erect habit.

Rate of flower opening: 2 to 3 days from bud to fully opened flower.

Flower longevity on plant: 3 to 6 days.

Approximate quantity of flowers per plant: About 60.

Persistent or self-cleaning: Self-cleaning.

Bud:

*Shape*.—Tubular.
*Length*.—About 4.0 cm.
*Diameter*.—About 0.7 cm.
*Color*.—RHS Yellow-green 145 B.

Flower size:

*Diameter*.—About 6 cm.
*Flower tube length*.—About 2.5 cm.
*Flower tube diameter at distal end*.—1.1 cm.
*Flower tube diameter at proximal end*.—0.3 cm.

Petals:

*Length from throat*.—About 2.5 cm.
*Width*.—About 3 cm.
*Quantity*.—5.
*Texture*.—Velvety.
*Apex*.—Blunt.
*Margin*.—Entire.

Color:

*When opening*.—Upper surface: RHS Violet-Blue 93 A. Lower surface: RHS Violet-Blue 94 D.

*Fully opened*.—Upper surface: RHS Violet-Blue 93 B. Lower surface: RHS Violet-Blue 94 D. Flower throat (inside): RHS White 155 B. Flower throat, vein: RHS Yellow-Green 144 B. Flower tube (outside): RHS White N 155 B. Flower tube, vein: RHS Yellow-Green 144 A.

Fading:

*Petals fading to*.—RHS Violet-Blue 93 C.

Calyx/sepals:

*Quantity per flower*.—5.

*Shape*.—Linear.

*Length*.—About 2 cm.

*Width*.—About 0.4 cm.

*Apex*.—Acute.

*Base*.—Cuneate.

*Margin*.—Entire.

*Texture*.—Velvety.

*Color*.—Upper Surface: RHS Green 137 A. Lower Surface: RHS Green 137 B.

Pedicel:

*Length*.—About 3 cm.

*Diameter*.—About 0.2 cm.

*Color*.—RHS Yellow-Green 144 A.

*Orientation*.—45 degrees.

Fragrance: None.

REPRODUCTIVE ORGANS

Stamens:

*Number*.—5.

*Filament length*.—About 2 cm.

Anthers:

*Length*.—About 0.1 cm.

*Shape*.—Rounded.

*Color*.—RHS White 155 A.

*Pollen*.—Color: RHS White-Yellow 158 A. Quantity: Plenty.

Pistil:

*Number*.—1.

*Length*.—About 2.1 cm.

*Style*.—Length: About 1.6 cm. Color: RHS Yellow-Green 145 B.

*Stigma*.—Shape: Rounded. Color: RHS Yellow-Green 145 A. Ovary Color: RHS Yellow-Green 144 C.

OTHER CHARACTERISTICS

Seeds and fruits: About 80 Brown, rounded seeds of about 0.5 mm diameter, per one brown, conical capsule. Tan-brown capsule and darker brown seeds not accurately measured with R.H.S. Colour chart.

Disease/pest resistance: Neither resistance nor susceptibility to the normal diseases and pests of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DPECLABRAY' as herein illustrated and described.

* * * * *